United States Patent [19]

Potenza

[11] Patent Number: 5,719,292
[45] Date of Patent: Feb. 17, 1998

[54] PROCESS FOR PREPARING A THIOETHER COMPOUND

[75] Inventor: Joan C. Potenza, Rush, N.Y.

[73] Assignee: Eastman Kodak Company, Rochester, N.Y.

[21] Appl. No.: 829,910

[22] Filed: Mar. 27, 1997

[51] Int. Cl.$^6$ .................. C07D 231/14; C07D 249/12
[52] U.S. Cl. .................. 548/262.4; 548/366.4; 548/367.1; 560/17; 562/427; 562/562; 564/162
[58] Field of Search ............... 548/366.4, 367.1, 548/262.4; 560/17; 562/427, 562; 564/162

[56] References Cited

U.S. PATENT DOCUMENTS

| | | | |
|---|---|---|---|
| 4,293,691 | 10/1981 | Furutachi et al. | 544/140 |
| 4,556,630 | 12/1985 | Furutachi et al. | 430/372 |
| 4,853,319 | 8/1989 | Krishnamurthy et al. | 430/387 |
| 4,912,024 | 3/1990 | Michno et al. | 430/544 |
| 5,151,343 | 9/1992 | Begley et al. | 430/382 |

FOREIGN PATENT DOCUMENTS

| | | |
|---|---|---|
| 59-37820 | 8/1982 | Japan . |
| 01-009972 | 7/1987 | Japan . |
| 01-186856 | 1/1988 | Japan . |
| 01-186859 | 1/1988 | Japan . |
| 02-111756 | 10/1988 | Japan . |
| 1-186858 | 7/1989 | Japan . |

*Primary Examiner*—Joseph McKane
*Attorney, Agent, or Firm*—Arthur E. Kluegel

[57] ABSTRACT

The invention provides a process for preparing a coupler compound having a thioether group at the coupling site comprising reacting in the presence of a base (a) a coupler compound having at least one hydrogen at the coupling site with (b) a mixed disulfide comprising either a tetrazole group or an oxadiazole group linked to one sulfur atom and an alkyl or aryl group linked to the other sulfur atom.

18 Claims, No Drawings

PROCESS FOR PREPARING A THIOETHER COMPOUND

FIELD OF THE INVENTION

This invention relates to a method for preparation of couplers for color photography which contain thioether groups at the active coupling position.

BACKGROUND OF THE INVENTION

In color photography using silver halide based light sensitive materials a color image is obtained by the reaction of a color coupler with the oxidation product of a color developing agent. Examples of suitable couplers and developers are described in James, T. H. *The Theory of the Photographic Process*, 4th Ed. MacMillan Publishing Co., Inc., (1977), Pp 337 et seq. The oxidized developer is formed upon development of exposed silver halide granules present in a gelatin emulsion layer which also contains the color image forming coupler. The oxidized developer and color coupler compound react to generate dye, of which the color image is formed. The color image forming materials or color couplers possess a site that is activated toward reaction with oxidized developer (the coupling site). The couplers have a hydrogen atom or a leaving group (coupling off group) at the activated site which is cleaved upon dye formation. Couplers with a coupling-off group to be cleaved theoretically require only two moles of silver halide to generate one mole of dye and are thus termed two equivalent couplers. Couplers with a hydrogen atom to be cleaved are correspondingly termed four equivalent couplers. The coupling off group may be selected solely for its reactivity and its passive effect on the resulting image after processing, or it may be selected so as to be a photographically useful group (PUG) that can serve an independent function such as carrying out color correction, assisting in the bleaching of unwanted silver, contributing to sharpness, or otherwise providing interimage effects. Another class of coupler compounds that couple with oxidized developer to release photographically useful groups are those which form either colorless species or dyes that are washed out during processing and thus not retained in the final image (U.S. Pat. No. 5,151,343). Thiol coupling off groups have been employed for all the above purposes and couplers which release them are valuable tools for obtaining desirable features in a photographic system (U.S. Pat. Nos. 4,556,630 and 4,853,319). Particularly useful coupler compounds are those which release a mercaptan upon coupling with oxidized developer, in particular, those in which the mercapto substituent is an alkyl thioether.

A variety of methods exist for the attachment of alkylthiol groups to the active position of a coupler. A stepwise method in which sulfur is first attached to the coupling position, followed by the alkyl group, is described in Japanese published application JO1-009972-A and U.S. Pat. No. 4,912,024 (eq. 1). Another variation is described in Japanese published application JO1-186859-A in which the anion of the thiol group is used to displace a leaving group in the coupling off position of the coupler (eq. 2). This requires a step in which the coupler is first halogenated. Another method of synthesis involves reaction of the unsubstituted coupler parent with a reagent which is a derivative of the thiol in which the sulfur is bound to a leaving group, X, and the thiol moiety serves as an electrophile (eq. 3). Some examples of these type of reagents are: sulfenyl halides 5 which are described in JO1-186856-A; thiolsulfonates 6, described in JO2-111756-A; S-alkylthioisothio ureas 7, described in U.S. Pat. No. 4,293,691 and JP 59-37820.

Mixed alkyl disulfides 8 are described in JO1-186858. In the process proposed, assymetric disulfides are proposed as a means of appending various mercapto groups to couplers. The compounds suggested have an alkyl sulfide coupled with a ring sulfide but the use of a mercaptotetrazole or an mercaptooxadiazole is never mentioned.

The stepwise methods (eq. 1 and 2) require more overall manipulation to arrive at the final product, resulting in lower throughput, higher waste volumes and higher overall costs. All involve initial formation of a derivative, either a di- or polysulfide or a material of the form COUP—S—X which must then be reduced to COUP—SH using either hydride reducing agents or metals. Hydride reagents present safety and handling problems in large scale production and metal reductions result in large volumes of environmentally hazardous solid waste, and can lead to unacceptably high levels of residual metals in the products. Metals can cause undesirable effects in the photographic system, as can the presence of residual thiol and sulfide intermediates. The method of eq. 2 involves halogenation of the coupler parent prior to reaction with the thiol anion. The halogenated coupler itself is photographically active and can cause problems if present as an impurity. Halogenated by-products often result when this method is used and bis chlorination of the active position is a particular problem when coupler parents other than naphthols are employed. (eg. pyrazalones, b-ketoamides, pyrazolotriazoles). Halogenated liquors and wastes must be disposed of and generally cannot be reclaimed.

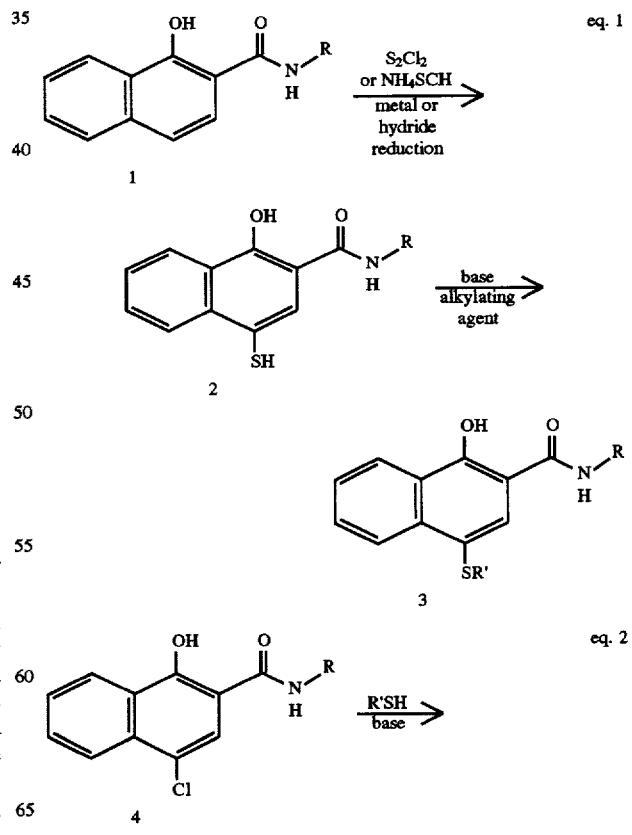

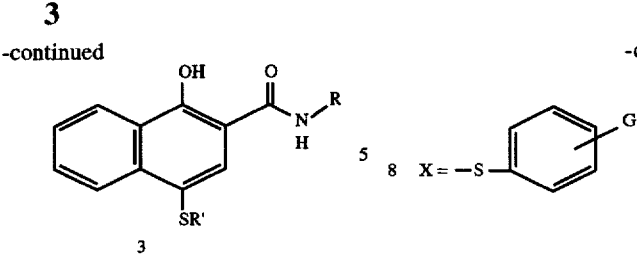

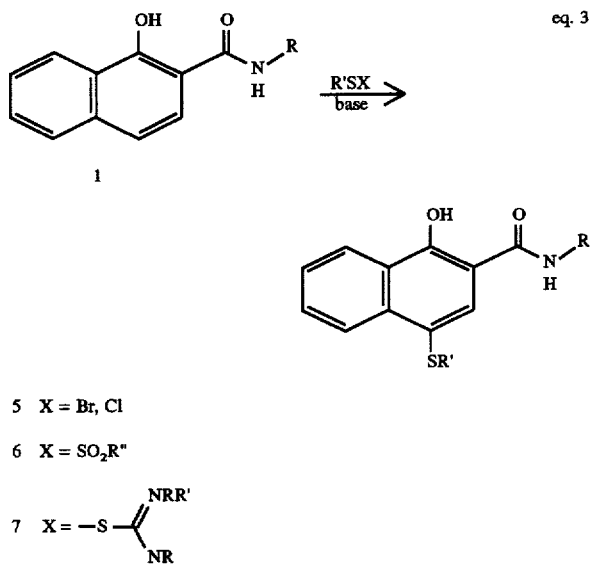

The mixed alkylthiourea disulfides require the handling of toxic thiourea and have been noted to be base unstable. They must be isolated by selective crystallization from an aqueous environment as their hydrochloride salts and cannot be prepared and used in-situ. A full equivalent of thiourea is eliminated as a leaving group and must be disposed of. (High aqueous solubility precludes recovery). J01-186858 describes the use of mixed alkyl-aryl disulfides as well as some heterocyclic examples. The synthetic examples described employ only one of the mixed disulfides disclosed, as shown in Scheme 1 below, in which the leaving entity is 2,4-dinitro-thiophenol, a highly colored material which rapidly oxidizes to its disulfide under the reaction conditions. This disulfide is capable of reacting with the coupler parent to produce an unwanted product which bears a 2,4-dinitrothiophenyl group in the coupling position. The remaining 2,4-dinitrophenyl

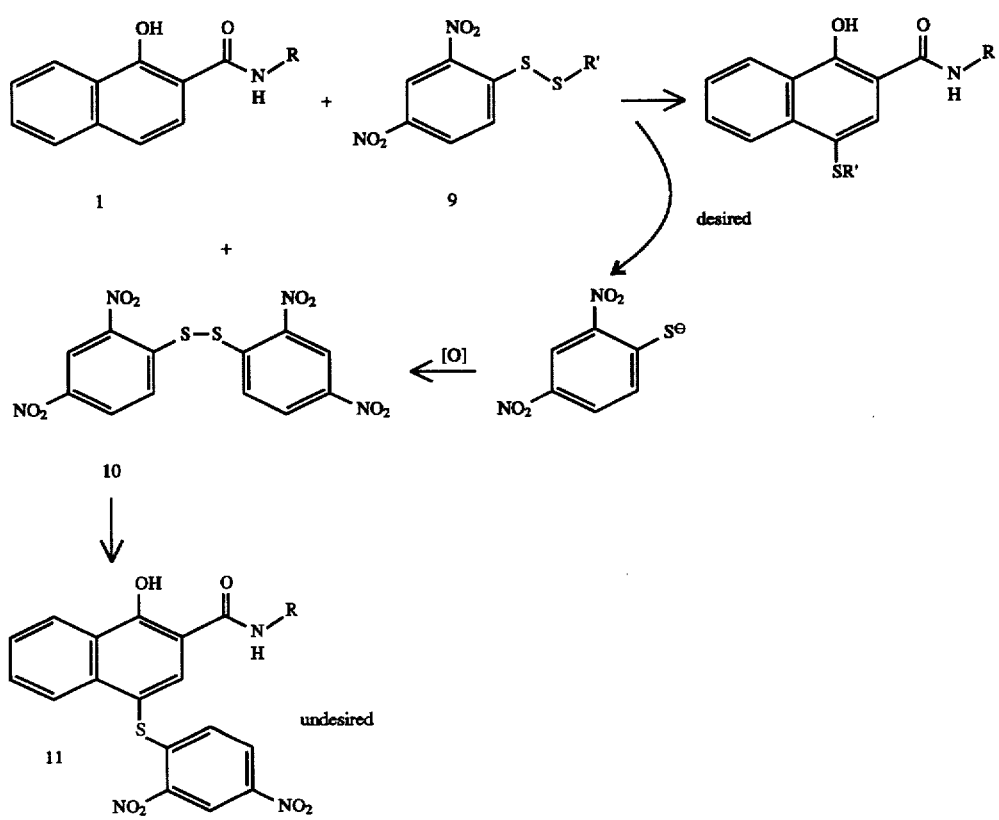

disulfide must be separated by chromatography from the desired product. The rapid oxidation of any of the aryl thiolate portions of the mixed disulfides is a general problem with this method, as is lack of selectivity in the bonding of one thiol component of the mixed disulfide over the other.

Mixed disulfides other than the 2,4-dinitrophenylthiol are mentioned in this patent, but serious difficulties were encountered in the attempted preparation and use of a selection of these. Compounds 12 and 13 could not be prepared using the methods cited in J01-186858. New methods had to be developed to prepare then just for comparison. Compound 12 was made and found to be inert toward a naphthol 4-equivalent coupler. It reacted with a pyrazalone coupler but the major product that formed resulted from transfer of the undesired aryl group onto the coupler parent. Compound 13 was made and found to react with pyrazalone couplers only and not naphthols.

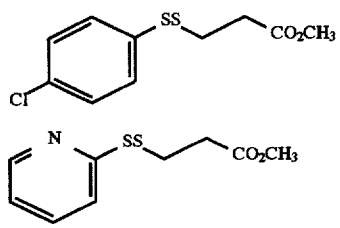

It is a problem to be solved to provide a process for synthesizing a coupler compound having a thioether group at the coupling site which process has good yields and is simple, safe, and environmentally friendly.

SUMMARY OF THE INVENTION

A process for preparing a coupler compound having a thioether group at the coupling site comprising reacting, in the presence of a base, (a) a coupler compound having at least one hydrogen at the coupling site; and (b) a mixed disulfide comprising either a tetrazole group or an oxadiazole group linked to one sulfur atom and an alkyl or aryl group linked to the other sulfur atom.

The process has good yields and is simple, safe, and environmentally friendly.

DETAILED DESCRIPTION OF THE INVENTION

The invention may be summarized as described in the preceding section. The process enables one to selectively append just the alkyl or aryl thio group to the coupler compound. The azole does not react to form an undesired side-product with the coupler. The azole does not spontaneously reoxidize to the disulfide and the resulting mercaptoazole can be completely removed. Azoles can be development inhibitors in photographic systems so it is important to be able to separate such materials from the coupler. If desired, the resulting mercaptoazole may be recovered from the reaction medium during work up of the desired product. The tetrazole can be recovered by partitioning it into a basic wash layer. If acid is then added to the aqueous wash layer, the tetrazole can be precipitated or extracted. Thus, the recovered tetrazole can then be converted back to mixed disulfide in a separate reaction.

The reaction of the invention is suitably carried out in an organic solvent. Suitable solvents include ethyl acetate, propyl acetate, dimethylformamide(DMF), acetonitrile, methylene chloride, acetone, toluene, methanol, isopropanol, and mixtures thereof. Ethyl acetate, propyl acetate, DMF and mixtures thereof, such as 4:1 ethyl acetate: DMF are preferred. The reaction is desirably substantially free of water.

The base may be any organic or inorganic base which will not unduly interfere with the reaction. Suitable examples are alkali metal acetate, bicarbonate, or carbonate, trialkyl amine such as triethylamine, tetramethyl guanidine, and dimethyl aniline. One or more equivalents of sodium acetate, bicarbonate and carbonate are preferred. The temperature of the reaction is suitably less than about 35° C. although higher temperatures up to the boiling point of the solvent may be employed.

The mixed disulfide reactant is comprised of a mercaptoazole "carrier" group and an alkyl- or aryl-thiol group which is the target to be appended to the coupler. In particular, the mercaptoazole is suitably a mercaptotetrazole or a mercaptooxadiazole. These azole compounds are effective in acting as an inert carrier for the thio compound to be appended to the coupler. The mercaptoazole compound may contain any substituents as desired to be appended to the coupler so long as they do not interfere with the reaction. The component to be appended may be a substituted alkyl or aryl group containing a substituent such as ester, hydroxy, carboxy, acyl, sulfonamido, alkoxy, acyamino etc.

Suitably, R has the formula:

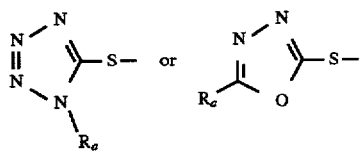

wherein $R_a$ is an alkyl or aryl group, conveniently a methyl, ethyl, t-butyl or a phenyl group.

As indicated, the coupler may be any coupler having a hydrogen atom at the coupling site, or such a compound which bears an active methylene group which is capable of ionizing to a nucleophillic state in the presence of a base. Such compounds include, for example, those derived from naphthols; phenols, pyrazoloazoles, pyrazolones, and acylacetanilides. Generic examples are:

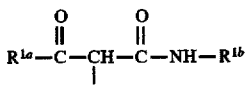

1A

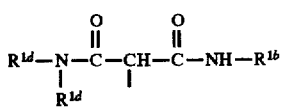

1B

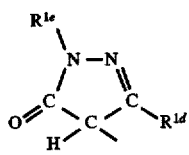

1C

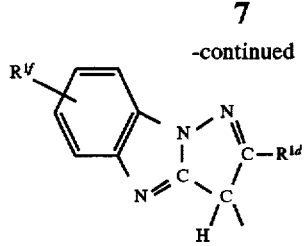
1D

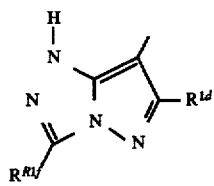
1E

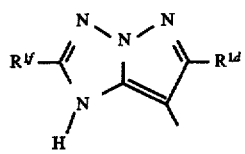
1F

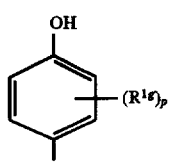
1G

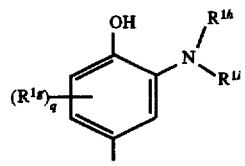
1H

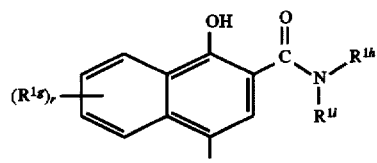
1I

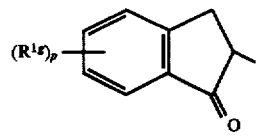
1J

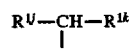
1K

A free bond from the coupling site in the above formulae indicates a position to which the coupling release group or coupling-off group is linked. In the above formulae, when $R^{1a}$, $R^{1b}$, $R^{1c}$, $R^{1d}$, $R^{1e}$, $R^{1f}$, $R^{1g}$, $R^{1h}$, $R^{1i}$, $R^{1j}$, or $R^{1k}$ contains a ballast or antidiffusing group, it is selected so that the total number of carbon atoms is from 8 to 32 and preferably from 10 to 22.

$R^{1a}$ represents an aliphatic- or alicyclic-hydrocarbon group, an aryl group, an alkoxyl group, or a heterocyclic group, and $R^{1b}$ and $R^{1c}$ each represents an aryl group or a heterocyclic group.

The aliphatic- or alicyclic hydrocarbon group represented by $R^{1a}$ preferably has at most 22 carbon atoms, may be substituted or unsubstituted, and aliphatic hydrocarbon may be straight or branched. Preferred examples of the substituent for these groups represented by $R^{1a}$ are an alkoxy group, an aryloxy group, an amino group, an acylamino group, and a halogen atom. These substituents may be further substituted with at least one of these substituents repeatedly. Useful examples of the groups as $R^{1a}$ include an isopropyl group, an isobutyl group, a tert-butyl group, an isoamyl group, a tert-amyl group, a 1,1-dimethyl-butyl group, a 1,1-dimethylhexyl group, a 1,1-diethylhexyl group, a dodecyl group, a hexadecyl group, an octadecyl group, a cyclohexyl group, a 2-methoxyisopropyl group, a 2-phenoxyisopropyl group, a 2-p-tert-butylphenoxyisopropyl group, an a-aminoisopropyl group, an a-(diethylamino)isopropyl group, an a-(succinimido) isopropyl group, an a-(phthalimido)isopropyl group, an a-(benzenesulfonamido)isopropyl group, and the like.

When $R^{1a}$, $R^{1b}$, or $R^{1c}$ is an aryl group (especially a phenyl group), the aryl group may be substituted. The aryl group (e.g., a phenyl group) may be substituted with groups having not more than 32 carbon atoms such as an alkyl group, an alkenyl group, an alkoxy group, an alkoxycarbonyl group, an alkoxycarbonylamino group, an aliphatic- or alicyclic-amido group, an alkylsulfamoyl group, an alkylsulfonamido group, an alkylureido group, an aralkyl group and an alkyl-substituted succinimido group. This phenyl group in the aralkyl group may be further substituted with groups such as an aryloxy group, an aryloxycarbonyl group, an arylcarbamoyl group, an arylamido group, an arylsulfamoyl group, an arylsulfonamido group, and an arylureido group.

The phenyl group represented by $R^{1a}$, $R^{1b}$, or $R^{1c}$ may be substituted with an amino group which may be further substituted with a lower alkyl group having from 1 to 6 carbon atoms, a hydroxyl group, —COOM and —SO$_2$M (M=H, an alkali metal atom, NH$_4$), a nitro group, a cyano group, a thiocyano group, or a halogen atom.

$R^{1a}$, $R^{1b}$, or $R^{1c}$ may represent substituents resulting from condensation of a phenyl group with other rings, such as a naphthyl group, a quinolyl group, an isoquinolyl group, a chromanyl group, a coumaranyl group, and a tetrahydronaphthyl group. These substituents may be further substituted repeatedly with at least one of above-described substituents for the phenyl group represented by $R^{1a}$, $R^{1b}$ or $R^{1c}$.

When $R^{1a}$ represents an alkoxy group, the alkyl moiety of the alkoxyl group can be a straight or branched alkyl group, an alkenyl group, a cycloalkyl group, or a cycloalkenyl group each having at most 32 carbon atoms, preferably at most 22 carbon atoms. These substituents may be substituted with groups such as halogen atom, an aryl group and an alkoxyl group to form a group having at most 32 carbon atoms.

When $R^{1a}$, $R^{1b}$, or $R^{1c}$ represents a heterocyclic ring, the heterocyclic group is linked to a carbon atom of the carbonyl group of the acyl group in a-acylacetamido or to a nitrogen atom of the amido group through one of the carbon atoms constituting the ring. Examples of such heterocyclic rings are thiophene, furan, pyran, pyrrole, pyrazole, pyridine, pyrazine, pyrimidine, pyridazine, indolizine, imidazole, thiazole, oxazole, triazine, thiadiazine and oxazine. These groups may further have a substituent or substituents in the ring thereof. Examples of the substituents include those defined for the aryl group represented by $R^{1a}$, $R^{1b}$ and $R^{1c}$.

In formula (1C), $R^{1e}$ is a group having at most 32 carbon atoms, preferably at most 22 carbon atoms, and it is a straight or branched alkyl group (e.g., a methyl group, an isopropyl group, a tert-butyl group, a hexyl group and a dodecyl group), an alkenyl group (e.g., an allyl group), a cycloalkyl group (e.g., a cyclopentyl group, a cyclohexyl group and a norbornyl group), an aralkyl group (e.g., a benzyl group and a b-phenylethyl group), or a cycloalkenyl group (e.g., a cyclopentenyl group and a cyoloalkenyl group). These groups may be further substituted with groups such as a halogen atom, a nitro group, a cyano group, an aryl group, an alkoxyl group, an aryloxy group, —COOM (M=H, an alkali metal atom, $NH_4$) an alkylthiocarbonyl group, an arylthiocarbonyl group, an alkoxycarbonyl group, an aryloxycarbonyl group, a sulfo group, a sulfamoyl group, a carbamoyl group, an acylamino group, a diacylamino group, a ureido group, a urethane group, a thiourethane group, a sulfonamide group, a heterocyclic group, an arylsulfonyl group, an alkylsulfonyl group, an arylthio group, an alkylthio group, an alkylamino group, a dialkylamino group, an anilino group, an N-arylanilino group, an N-alkylanilino group, an N-acylanilino group, a hydroxyl group, and a mercapto group.

Furthermore $R^{1e}$ may represent an aryl group (e.g., a phenyl group and an a- or b-naphthyl group). This aryl group may be substituted with at least one group. Examples of such substituents are an alkyl group, an alkenyl group, a cycloalkyl group, an aralkyl group, a cycloalkenyl group, a halogen atom, a nitro group, a cyano group, an aryl group, an alkoxy group, an aryloxy group, —COOM (M=H, an alkali metal atom, $NH_4$), an alkoxycarbonyl group, an aryloxycarbonyl group, a sulfo group, a sulfamoyl group, a carbamoyl group, an acylamino group, a diacylamino group, a ureido group, a urethane group, a sulfonamido group, a heterocyclic group, an arylsulfonyl group, alkylsulfonyl group, an arylthio group, an alkylthio group, an alkylamino group, a dialkylamino group, an anilino group, an N-alkylanilino group, an N-arylanilino group, an N-acylanilino group, a hydroxyl group, and a mercapto group. More preferred as $R^{1e}$ is a phenyl group which is substituted with at least one of the groups such as an alkyl group, an alkoxyl group, and a halogen atom in at least one ortho-position, because it decreases color formation due to light or heat of the coupler remaining in a film member.

Furthermore, $R^{1e}$ may represent a heterocyclic group (e.g., 5- or 6-membered heterocyclic rings and condensed heterocyclic groups containing at least one hetero atom i.e., a nitrogen atom, an oxygen atom or a sulfur atom such as a pyridyl group, a quinolyl group, a furyl group, a benzothiazolyl group, an oxazolyl group, an imidazolyl group, and a naphthooxazolyl group), a heterocyclic group substituted with a group as listed for the above aryl group represented by $R^{1e}$, an aliphatic, alicyclic or aromatic acyl group, an alkylsulfonyl group, an arysulfonyl group, an alkylcarbarmoyl group, an arylcarbamoyl group, an alkylthiocarbanoyl group or an arylthiocarbamoyl group.

$R^{1d}$ represents a hydrogen atom, and represents groups having at most 32 carbon atoms, preferably at most 22 carbon atoms, such as a straight or branched alkyl group, an alkenyl group, a cycloalkyl group, an aralkyl group, a cycloalkenyl group (these groups may have a substituent or substituents as listed for $R^{1e}$), an aryl group, a heterocyclic group (these groups may have a substituent or substituents as listed for $R^{1e}$ an alkoxycarbonyl group (e.g., a methoxycarbonyl group, an ethoxycarbonyl group, and a stearyloxycarbonyl group), an aryloxycarbonyl group (e.g., a phenoxycarbonyl group and a naphthoxycarbonyl group), an aralkyloxycarbonyl group (e.g., a benzyloxycarbonyl group), an alkoxy group (e.g., a methoxy group, an ethoxy group, and a heptadecyloxy group), an aryloxy group (e.g., a phenoxy group and a tolyloxy group), an alkylthio group (e.g., an ethylthio group and a dodecylthio group), an arylthio group (e.g., a phenylthio group and an a-naphthylthio group), —COOM(M=H alkali metal atom $NH_4$), an acylamino group, an acetylamino group and a 3-[(2,4-di-tert-amylphenoxy)acetamido]benzamido group), a diacylamino group, an N-alkylacylamino group (e.g., an N-methylpropionamido group), an N-arylacylamino group (e.g., an N-phenylacetamido group), a ureido group, a substituted ureido group (e.g., an N-arylureido group, and an N-alkylureido group), a urethane group, a thiourethane group, an arylamino group (e.g., a phenylamino group, an N-methylanilino group, a di-phenylamino group, an N-acetylanilino group, and a 2-chloro-5-tetradecaneamidoanilino group), an alkylamino group (e.g., an n-butylamino group, a methylamino group and a cyclohexylamino group), a cycloamino group (e.g., a piperidino group, and a pyrrolidino group), a heterocyclic amino group (e.g., a 4-pyridylamino group and a 2-benzooxazolidyl amino group), an alkylcarbonyl group (e.g., a methylcarbonyl group), an arylcarbonyl group (e.g., a phenylcarbonyl group), a sulfonamido group (e.g., an alkylsulfonamido group and an arylsulfonamido group), a carbamoyl group (e.g., an ethylcarbamoyl group, a dimethylcarbamoyl group an N-methyl-N-phenylcarbamoyl group and an N-phenylcarbamoyl group), a sulfamoyl group (e.g., an N-alkylsulfamoyl group, an N,N-dialkylsulfamoyl group, an N-arylsulfamoyl, an N-alkyl-N-arylsulfamoyl group, and an N,N-diarylsulfamoyl group), a cyano group, a hydroxyl group, a mercapto group, a halogen atom, or a sulfo group.

$R^{1f}$ represents a hydrogen atom, and represents groups having at most 32 carbon atoms, preferably at most 22 carbon atoms, such as a straight or branched alkyl group, an alkenyl group, a cycloalkyl group, an aralkyl group, or a cycloalkenyl group. These groups may be substituted with a group or groups as listed for $R^{1e}$.

$R^{1f}$ may be an aryl group or a heterocyclic group. These groups may be substituted with a group or groups as listed for $R^{1e}$.

$R^{1f}$ may be a cyano group, an alkoxyl group, an aryloxy group, a halogen atom, —COOM(M=H, an alkali metal atom, $NH_4$), an alkoxycarbonyl group, an aryloxycarbonyl group, an acyloxy group, a sulfo group, a sulfamoyl group, a carbarmoyl group, an acylamino group, a diacylamino group, a ureido group, a urethane group, a sulfonamido group, an arylsulfonyl group, an alkylsulfonyl group, an urylthio group, an alkylthio group, an alkylamino group, a dialkylamino group, an anilino group, an N-aryl-anilino group, an N-alkylanilino group, an N-acylanilino group, a hydroxyl group, or a mercapto group.

$R^{1g}$, $R^{1h}$, $R^{1i}$ each represents a group as is conventionally used in 4-equivalent phenol or a-naphthol couplers $R^{1g}$, $R^{1h}$ and $R^{1i}$ each may have at most 32 carbon atoms, and preferably at most 22 carbon atoms.

More specifically, $R^{1g}$ represents a hydrogen atom, a halogen atom, an alkoxycarbonylamino group, an aliphatic or alicyclic-hydrocarbon group, an N-arylureido group, an acylamino group, a group —$R^{11}$ or a group —S—$R^{11}$ (wherein $R^{11}$ is an aliphatic- or alicyclic-hydrocarbon radical). When two or more of the groups of $R^{1g}$ are contained in one molecule they may be different, and the aliphatic- and alicyclic-hydrocarbon radical may be substituted. In a case that these substituents contain an aryl group, the aryl group may be substituted with a group or groups as listed for $R^{1e}$.

$R^{1h}$ and $R^{1i}$ each represents a group selected from an aliphatic- or alicyclic-hydrocarbon radial, an aryl group, and a heterocyclic group, or one of $R^{1h}$ and $R^{1i}$ may be hydrogen atom. The above groups may be substituted. $R^{1h}$ and $R^{1i}$ may combine together to form a nitrogen-containing heterocyclic nucleus.

The aliphatic- and alicyclic-hydrocarbon radical may be saturated or unsaturated, and the aliphatic hydrocarbon may be straight or branched. Preferred examples are an alkyl group (e.g., a methyl group, an ethyl group, an isopropyl group, a butyl group, a tert-butyl group, an isobutyl group, a dodecyl group, an octadecyl group, a cyclobutyl group and a cyclohexyl group), and an alkenyl group (e.g., an alkyl group and an octenyl group). Typical examples of the aryl group are a phenyl group and a naphthyl group, and typical examples of the heterocyclic radical are a pyridinyl group, a quinolyl group, a thienyl group, a piperidyl group, and an imidazolyl group. Groups to be introduced in these aliphatic hydrocarbon radical, aryl group and heterocyclic radical include a halogen atom, a nitro group, a hydroxyl group, a carboxyl group, an amino group, a substituted amino group, a sulfo group, an alkyl group, an alkenyl group, an aryl group, a heterocyclic group, an alkoxy group, an aryloxy group, an arylthio group, an arylazo group, an acylamino group, a carbamoyl group, an ester group, an acyl group, an acyloxy group, a sulfonamido group, a sulfamoyl group, a sulfonyl group, and a morpholino group.

p is an integer of 1 to 4, q is an integer of 1 to 3, and r is an integer of 1 to 5.

$R^{1j}$ represents a group having at most 32 carbon atoms and preferably at most 22 carbon atoms. $R^{1j}$ represents an arylcarbonyl group, an alkanoyl group, an alkanecarbamoyl group, an alkoxycarbonyl group, or an aryloxycarbonyl group. These groups may be substituted with groups such as an alkoxyl group, an alkoxycarbonyl group, an acylamino group, an alkylsulfamoyl group, an alkylsulfonamido group, an alkylsuccinimide group, a halogen atom, a nitro group, a carboxyl group, a nitrile group, an alkyl group, and an aryl group.

$R^{1k}$ represents groups having at most 32 carbon atoms, and preferably at most 22 carbon atoms. $R^{1k}$ represents an arylcarbonyl group, an alkanoyl group, an arylcarbamoyl group, an alkanecarbamoyl group, an alkoxycarbonyl group, and aryloxycarbonyl group, and arylsulfonyl group, an arylsulfonyl group, an aryl group, or a 5- or 6-membered heterocyclic group (containing a hetero atom selected from a nitrogen atom, an oxygen atom, and a sulfur atom, e.g., a triazolyl group, an imidazolyl group, a phthalamido group, a succinamido group, a furyl group, a pyridyl group, and a benzotriazolyl group). These groups may be substituted with a group or groups as listed for $R^{1j}$.

The above described substituted groups in formulae 1A–1K may be further substituted repeatedly once, twice or more with a group selected from the same group of the substituents to form substituted groups having preferably at most 32 carbon atoms.

In the reaction, it is desirable that the molar ratio of base to the coupler is in the range of 1–2.5:1. Further, the mole ratio of mixed disulfide to coupler is preferably in the range of 1–2.5:1.

One method of preparing a mixed azole disulfide is the following:

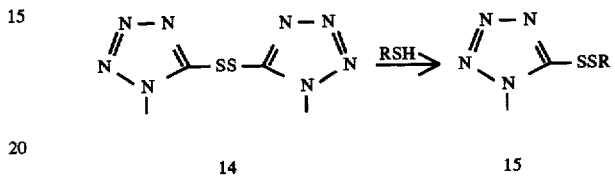

14  15

Another more efficient method is one in which only one equivalent of the azole is required.

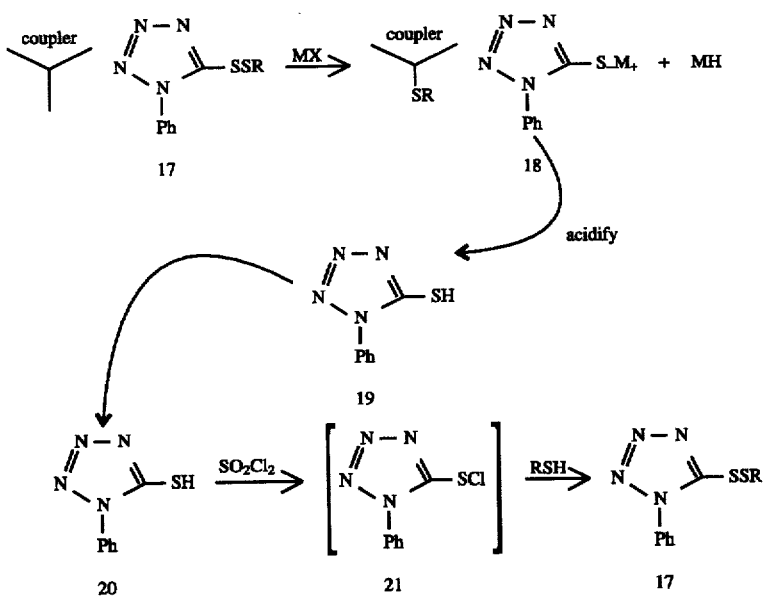

The sulfenyl halide is formed efficiently by treatment with sulfuryl chloride at room temperature. After de-gassing of the solution, the aliphatic thiol is added to generate the mixed azole disulfide. The formation of symmetrical disulfide can be managed through control of reaction time, temperature and reaction stoichiometry. This is important because the symmetrical disulfide can react with the 4-equivalent coupler to form mercaptotetrazole bearing impurities which would are highly undesirable. In practice, the formation of these materials can be kept below the level at which problems occur in a photographic system (less than or equal to 0.2% by HPLC). The mixed disulfides described herein show excellent selectivity in their reactions with photographic couplers of all classes. Of the possible heterocyclic moieties one might consider, only the oxadiazole-mixed disulfides showed a pattern of reactivity similar to the tetrazole species.

Table I provides examples of mixed azole disulfides that can be used in the process of the invention.
TABLE I
MIXED DISULFIDES
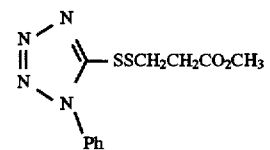
22
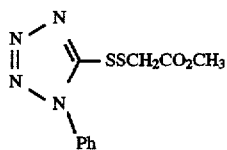
23
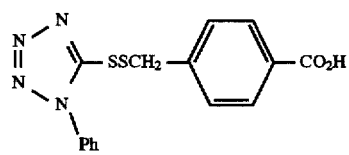
24
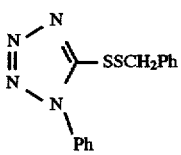
25
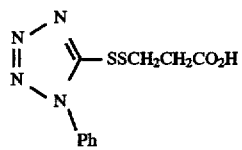
26
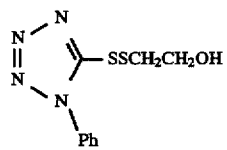
27
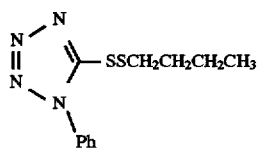
28
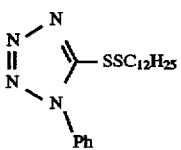
29
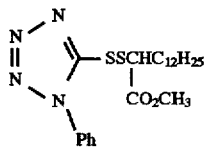
30
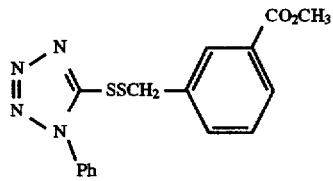
31
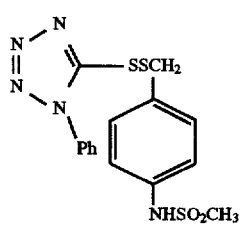
32
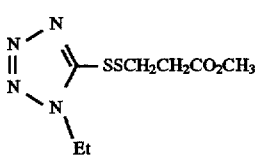
33
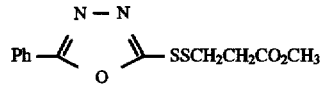
34
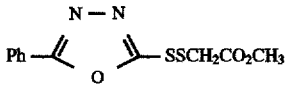
35

TABLE I-continued
MIXED DISULFIDES
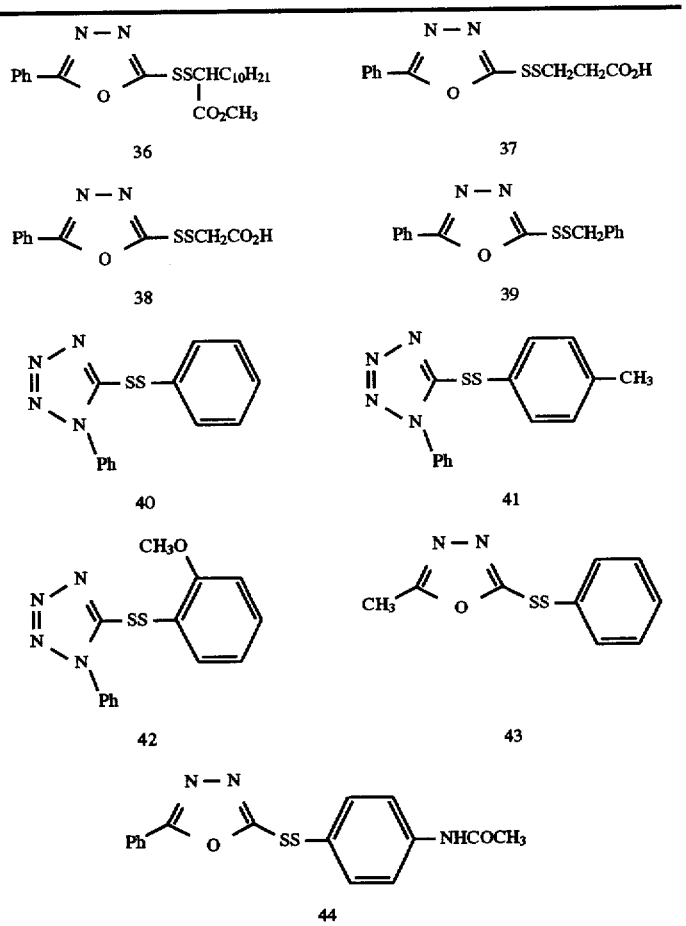
Table II shows examples of couplers that can be made by the process of the invention.
TABLE II
COUPLERS
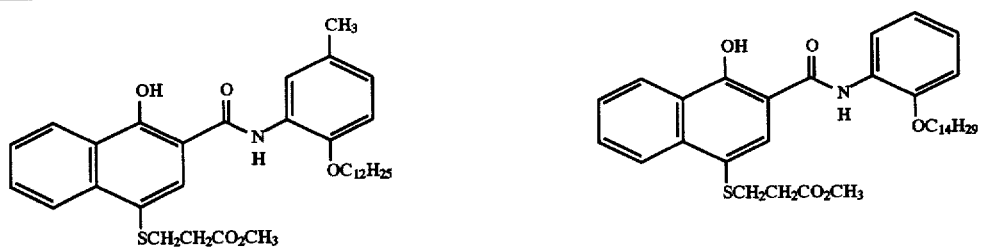

TABLE II-continued
COUPLERS
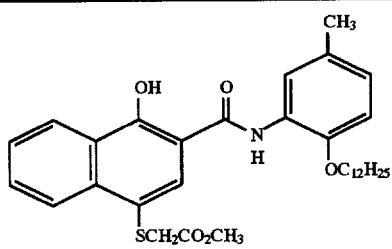
C-3
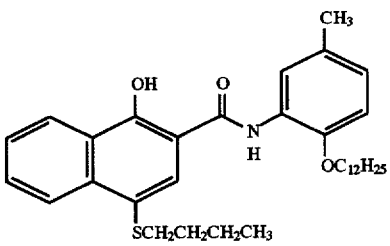
C-4
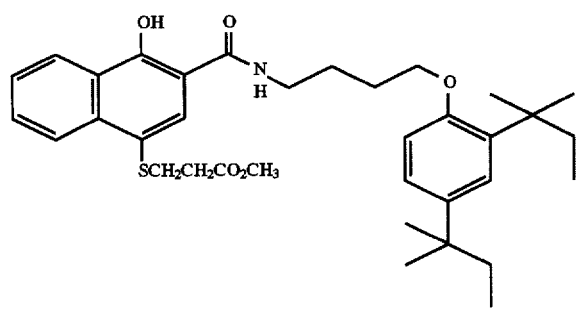
C-5
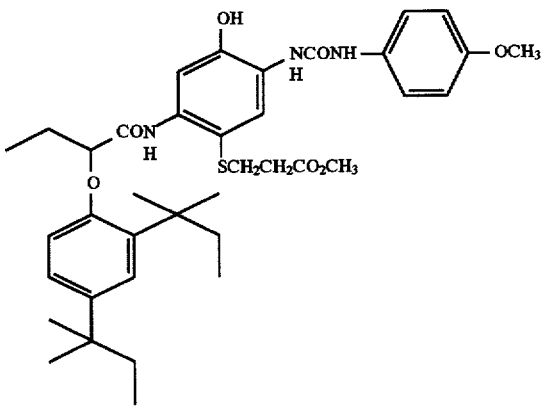
C-6
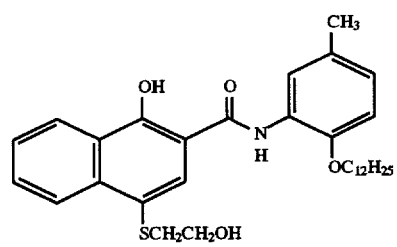
C-7
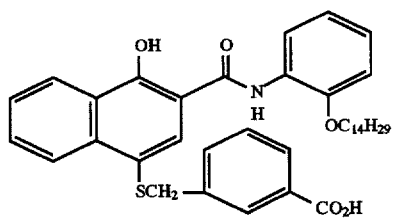
C-8
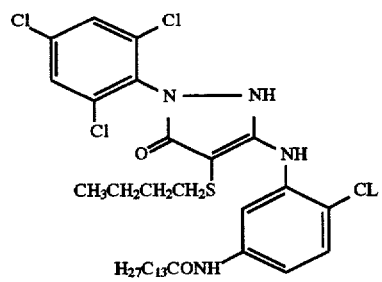
C-9
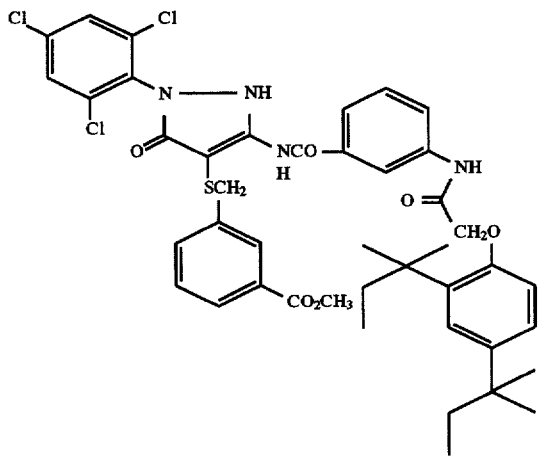
C-10

TABLE II-continued
COUPLERS
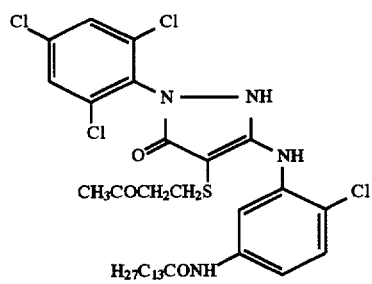
C-11
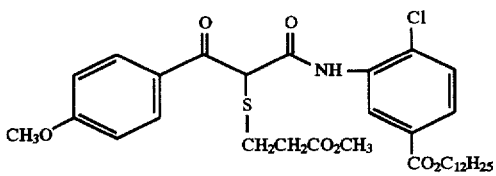
C-12
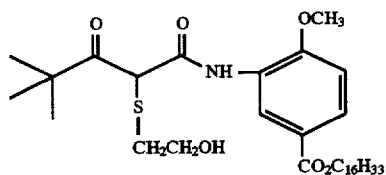
C-13
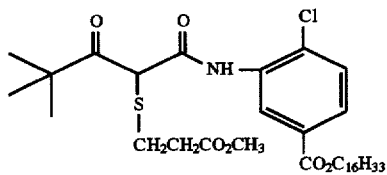
C-14
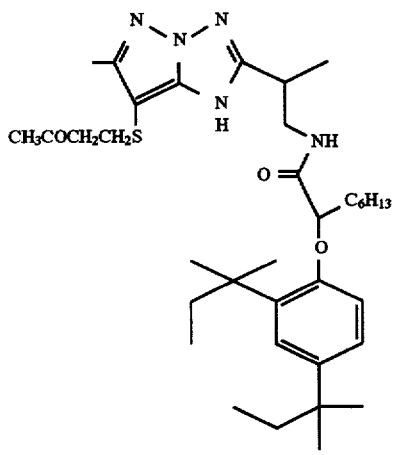
C-15
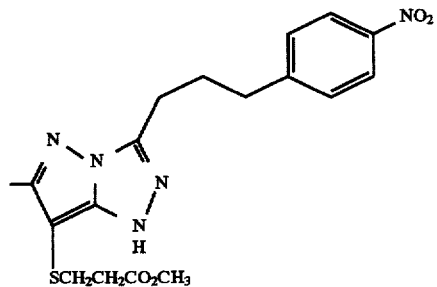
C-16
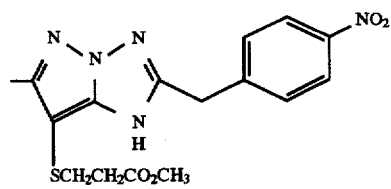
C-17
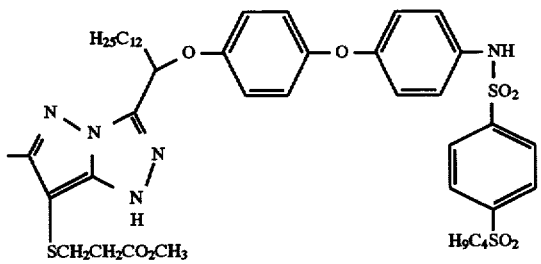
C-18

TABLE II-continued
COUPLERS

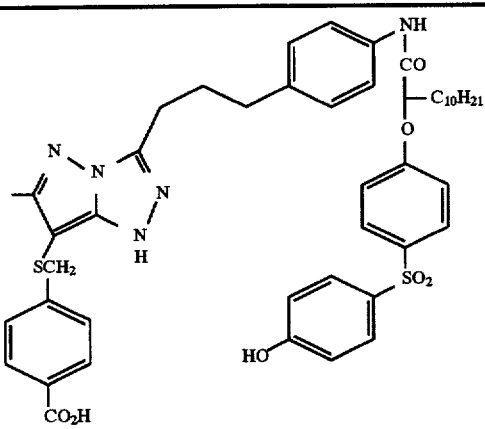

C-19

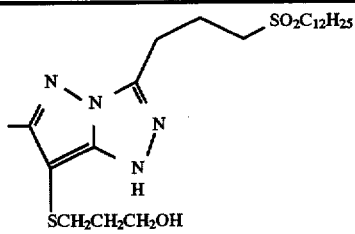

C-20

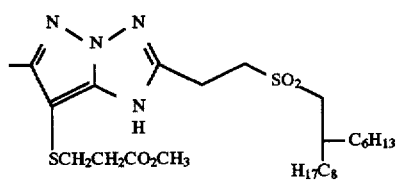

C-21

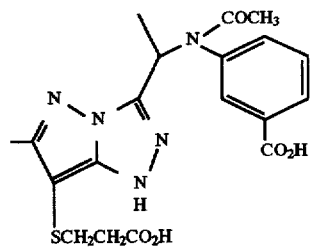

C-22

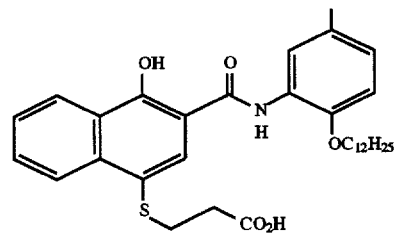

C-23

Unless otherwise specifically stated, substituent groups which may be substituted on molecules herein include any groups, whether substituted or unsubstituted. When the term "group" is applied to the identification of a substituent containing a substitutable hydrogen, it is intended to encompass not only the substituent's unsubstituted form, but also its form further substituted with any group or groups as herein mentioned. Suitably, the group may be halogen or may be bonded to the remainder of the molecule by an atom of carbon, silicon, oxygen, nitrogen, phosphorous, or sulfur. The substituent may be, for example, halogen, such as chlorine, bromine or fluorine; nitro; hydroxyl; cyano; carboxyl; or groups which may be further substituted, such as alkyl, including straight or branched chain alkyl, such as methyl, trifluoromethyl, ethyl, t-butyl, 3-(2,4-di-t-pentylphenoxy)propyl, and tetradecyl; alkenyl, such as ethylene, 2-butene; alkoxy, such as methoxy, ethoxy, propoxy, butoxy, 2-methoxyethoxy, sec-butoxy, hexyloxy, 2-ethylhexyloxy, tetradecyloxy, 2-(2,4-di-t-pentylphenoxy) ethoxy, and 2-dodecyloxyethoxy; aryl such as phenyl, 4-t-butylphenyl, 2,4,6-trimethylphenyl, naphthyl; aryloxy, such as phenoxy, 2-methylphenoxy, alpha- or beta-naphthyloxy, and 4-tolyloxy; carbonamido, such as acetamido, benzamido, butyramido, tetradecanamido, alpha-(2,4-di-t-pentyl-phenoxy)acetamido, alpha-(2,4-di-t-pentylphenoxy) butyramido, alpha-(3-pentadecylphenoxy)-hexanamido, alpha-(4-hydroxy-3-t-butylphenoxy)-tetradecanamido, 2-oxo-pyrrolidin-1-yl, 2-oxo-5-tetradecylpyrrolin-1-yl, N-methyltetradecanamido, N-succinimido, N-phthalimido, 2,5-dioxo-1-oxazolidinyl, 3-dodecyl-2,5-dioxo-1-imidazolyl, and N-acetyl-N-dodecylamino, ethoxycarbonylamino, phenoxycarbonylamino, benzyloxycarbonylamino, hexadecyloxycarbonylamino, 2,4-di-t-butylphenoxycarbonylamino, phenylcarbonylamino, 2,5-(di-t-pentylphenyl) carbonylamino, p-dodecyl-phenylcarbonylamino, p-toluycarbonylamino, N-methylureido, N,N-dimethylureido, N-methyl-N-dodecylureido, N-hexadecylureido, N,N-dioctadecylureido, N,N-dioctyl-N'-ethylureido, N-phenylureido, N,N-diphenylureido, N-phenyl-N-p-toluylureido, N-(m-hexadecylphenyl)ureido, N,N-(2,5-di-t-pentylphenyl)-N'-ethylureido, and t-butylcarbonamido; sulfonamido, such as methylsulfonamido, benzenesulfonamido, p-toluylsulfonamido, p-dodecylbenzenesulfonamido, N-methyltetradecylsulfonamido, N,N-dipropyl-sulfamoylamino, and hexadecylsulfonamido; sulfamoyl, such as N-methylsulfamoyl, N-ethylsulfamoyl, N,N-dipropylsulfamoyl, N-hexadecylsulfamoyl, N,N-dimethylsulfamoyl; N-[3-(dodecyloxy)propyl]sulfamoyl, N-[4-(2,4-di-t-pentylphenoxy)butyl]sulfamoyl, N-methyl-N-tetradecylsulfamoyl, and N-dodecylsulfamoyl; carbamoyl, such as N-methylcarbamoyl, N,N-dibutylcarbamoyl, N-octadecylcarbamoyl, N-[4-(2,4-di-t-pentylphenoxy)butyl]carbamoyl, N-methyl-N-tetradecylcarbamoyl, and N,N-dioctylcarbamoyl; carbonyl, such as acetyl, (2,4-di-t-amylphenoxy)acetyl, phenoxycarbonyl, p-dodecyloxyphenoxycarbonyl methoxycarbonyl, butoxycarbonyl, tetradecyloxycarbonyl, ethoxycarbonyl, benzyloxycarbonyl, 3-pentadecyloxycarbonyl, and dodecyloxycarbonyl; sulfonyl, such as methoxysulfonyl, octyloxysulfonyl, tetradecyloxysulfonyl, 2-ethylhexyloxysulfonyl, phenoxysulfonyl, 2,4-di-t-pentylphenoxysulfonyl, methylsulfonyl, octylsulfonyl, 2-ethylhexylsulfonyl, dodecylsulfonyl, hexadecylsulfonyl, phenylsulfonyl, 4-nonylphenylsulfonyl, and p-toluylsulfonyl; sulfonyloxy, such as dodecylsulfonyloxy, and hexadecylsulfonyloxy; sulfinyl, such as methylsulfinyl, octylsulfinyl, 2-ethylhexylsulfinyl, dodecylsulfinyl, hexadecylsulfinyl, phenylsulfinyl, 4-nonylphenylsulfinyl, and p-toluylsulfinyl; thio, such as ethylthio, octylthio, benzylthio, tetradecylthio, 2-(2,4-di-t-pentylphenoxy)ethylthio, phenylthio, 2-butoxy-5-t-octylphenylthio, and p-tolylthio; acyloxy, such as acetyloxy, benzoyloxy, octadecanoyloxy, p-dodecylamidobenzoyloxy, N-phenylcarbamoyloxy, N-ethylcarbamoyloxy, and cyclohexylcarbonyloxy; amine, such as phenylanilino, 2-chloroanilino, diethylamine, dodecylamine; imino, such as 1 (N-phenylimido)ethyl, N-succinimido or 3-benzylhydantoinyl; phosphate, such as dimethylphosphate and ethylbutylphosphate; phosphite, such as diethyl and dihexylphosphite; a heterocyclic group, a heterocyclic oxy group or a heterocyclic thio group, each of which may be substituted and which contain a 3 to 7 membered heterocyclic ring composed of carbon atoms and at least one hereto atom selected from the group consisting of oxygen, nitrogen and sulfur, such as 2-furyl, 2-thienyl, 2-benzimidazolyloxy or 2-benzothiazolyl; quaternary ammonium, such as triethylammonium; and silyloxy, such as trimethylsilyloxy.

If desired, the substituents may themselves be further substituted one or more times with the described substituent groups. The particular substituents used may be selected by those skilled in the art to attain the desired photographic properties or a specific application and can include, for example, hydrophobic groups, solubilizing groups, blocking groups, releasing or releasable groups, etc. Generally, the above groups and substituents thereof may include those having up to 48 carbon atoms, typically 1 to 36 carbon atoms and usually less than 24 carbon atoms, but greater numbers are possible depending on the particular substituents selected.

SYNTHETIC EXAMPLES

Example 1—Coupler C-1 or C-23 from mixed disulfide 22

Preparation of mixed disulfide 22

To a stirred solution of phenylmercaptotetrazole 19 (6.675 g, 0.0375 mol.) in 85 mL of ethyl acetate at 25° C. was added sulfuryl chloride (6.33 g, 0.046 mol.), dropwise, over 10 min. The resulting yellow solution was stirred at 25° C. for 30 min. The solution was then placed slowly under aspirator vacuum to draw off dissolved gasses. A 20° C. water bath was placed under the reaction flask and a dry ice cooled receiver was used to collect distillate. Approx. ¼ of the original solvent volume was collected in the receiver and then the flask was vented to nitrogen. The solvent was replenished to it's original level and the cooling bath temperature was adjusted to 15° C. To the mixture was added methyl-3-mercaptopropionate (4.5 g, 0.0375 mol.) dropwise at such a rate to keep the temperature at 25° C. or less. (approx. 15 min.) The mixture was stirred 30 min. then placed under vacuum as before for 15 min. to degass. 50 mL of cold water was then added all at once, with rapid stirring, to quench the mixture. It was poured into a separatory funnel and the aqueous layer removed. The organic layer was washed successively with 2 50 mL portions of 10% bicarbonate and one 50 mL portion of saturated brine, then dried over magnesium sulfate and filtered. Stripping of solvent provided 9.55 g (86%) mixed disulfide 22 as a mobile yellow oil, 95% by HPLC, M/e=296. NMR (CDCl$_3$): δ7.6, s, 5H, 3.7, s, 3H, 3.3, t, 2H, 2.9, t, 2H).

Preparation of C-1 and C-23 from mixed disulfide 22:

To a stirred solution of mixed disulfide 22 (9.55 g, 0.0322 mol.) in 100 ml 4:1 ethyl acetate:DMF was added the naphthol 4-equivalent coupler (13.83 g, 0.03 mol.) followed by potassium acetate (6.62 g, 0.067 mol.). The mixture was stirred at ambient temperature for 6 to 8 hr or until judged complete by TLC. The mixture was warmed to 45° C. to dissolve the precipitated product, then washed successively at 45 C. with 50 mL of water, 2×50 mL of 10% sodium bicarbonate and 50 mL saturated brine. Solvent removal by rotary evaporation provided 14.93 g (86%) of the ester product C-1 as a fluffy white solid. The product exhibited spectral properties consistent with the desired material. After hydrolysis and crystallization, Coupler C-23 was obtained as a white solid, 98–99% by HPLC. The product exhibited spectral properties consistent with the desired material. M/e=579. NMR(CDCl$_3$) δ8.9, s 1H, 8.5, m, 2H, 8.3, s, 1H, 7.9, s, 1H, 7.7, t, 1H, 7.6, t, 1H, 7.3, s, 1H, 6.9, m, 2H, 4.1, t, 2H, 3.1, t, 2H, 2.4, s, 3H, 1.9, m, 2H, 1.6, m, 2H, 1.2, m, 14H, 0.9, t, 3H Example 2—Coupler C-17 from mixed disulfide 22

A solution of mixed disulfide 22 (0.782 g, 0.0026 mol.), the 4-equivalent analogue of coupler C-17 (0.50 g, 0.0022 mol.), and potassium acetate (0.47 g, 0.0048 mol.) in 25 mL of 4:1 ethyl acetate: DMF was stirred at room temperature overnight. It was diluted with ethyl acetate, washed with 25 mL of water, two 25 mL portions of 10% bicarbonate solution, 25 mL of saturated brine, dried over magnesium sulfate, filtered and concentrated by rotary evaporation to provide an oil. Trituration with heptane provided a solid which was collected and recrystallized from toluene/ethyl acetate to yield 0.35 g (45%) of C-17 as a yellow crystalline solid which exhibited spectral properties consistent with the desired product. M/e=346. NMR(CDCl$_3$) δ57.0, d, 2H, 6.5, d, 2H, 3.9, s, 2H, 3.4, s, 3H, 2.7, t, 2H, 2.4, t, 2H, 2.2, s, 3H.

Example 3—Coupler C-1 from mixed disulfide 34

To a stirred solution of mixed disulfide 34( 1.77 g, 0.006 mol.) in 4:1 ethyl acetate: DMF (25 mL) was added. The 4-equivalent analogue of coupler C-1 (2.30 g, 0.005 mol.), followed by potassium acetate (1.08 g, 0.011 mol.) and the resulting solution was stirred for 6 h at room temperature. It was diluted with 25 mL ethyl acetate, 20 mL of water and warmed to 45° C. The layers were separated and the 45° C. organic layer was washed with two portions of 10% sodium bicarbonate, saturated brine, dried over magnesium sulfate, filtered and concentrated under vacuum to provide 2.36 g of C-1 (81.5%) of as a tan solid which was analytically identical with previously characterized material.

The entire contents of any patents and other publications referred to in this specification are incorporated herein by reference.

What is claimed is:

1. A process for preparing a coupler compound having a thioether group at the coupling site comprising reacting, in the presence of a base,
   (a) a coupler compound having at least one hydrogen at the coupling site; and
   (b) a mixed disulfide comprising either a tetrazole group or an oxadiazole group linked to one sulfur atom and an alkyl or aryl group linked to the other sulfur atom.

2. The process of claim 1 wherein the mixed disulfide has the formula (I)

wherein R is a tetrazole group or an oxadiazole group and R' is an alkyl or aryl group.

3. The process of claim 1 wherein the base is selected from the group consisting of alkali metal acetates, bicarbonates, carbonates, hydroxides, alkoxides and amines.

4. The process of claim 1 wherein the base is selected from sodium acetate, potassium acetate, sodium bicarbonate, potassium bicarbonate, sodium carbonate, potassium carbonate, triethylamine, tetramethylguanidine, diisopropylethylamine, and dimethylaniline.

5. The process of claim 1 wherein the medium in which the reaction takes place comprises an organic solvent.

6. The process of claim 5 wherein the reaction medium is substantially free of water.

7. The process of claim 5 wherein the organic solvent is selected from the group consisting of ethyl acetate, propyl acetate, dimethylformamide, acetonitrile, methylene chloride, acetone, toluene, methanol, ethanol, and isopropanol.

8. The process of claim 7 wherein the reaction medium comprises ethyl acetate or propyl acetate in combination with dimethylformamide.

9. The process of claim 1 wherein the molar ratio of base to coupler is 2–3.5:1.

10. The process of claim 1 wherein the molar ratio of mixed disulfide to coupler is 1–2.5:1.

11. The process of claim 1 wherein the coupler is selected from the group consisting of magenta, yellow, and cyan dye-forming couplers.

12. The process of claim 1 wherein the coupler is selected from the group consisting of acylacetanilides, pyrazolones, pyrazoloazoles, phenols, and naphthols.

13. The process of claim 1 wherein the coupler is a naphthol.

14. The process of claim 2 wherein R has the formula:

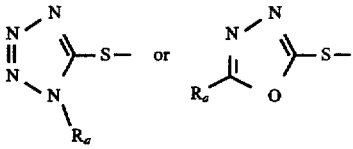

wherein $R_a$ is an alkyl or aryl group.

15. The process of claim 14 wherein $R_a$ is a methyl, ethyl, t-butyl or a phenyl group.

16. The process of claim 2 wherein R' is an aryl group.

17. The process of claim 2 wherein R' is an alkyl group.

18. The process of claim 17 wherein R' is a propionic ester or acid group.

* * * * *